(12) United States Patent (10) Patent No.: US 8,682,442 B2
McAdams (45) Date of Patent: Mar. 25, 2014

(54) ELECTRICAL WOUND HEALING SYSTEM AND METHOD

(75) Inventor: Eric Thomas McAdams, Whitehead (GB)

(73) Assignees: University of Ulster, County Londonberry (GB); Institut National des Sciences Appliquees de Lyon, Villeurbanne (FR)

( * ) Notice: Subject to any disclaimer, the term of this patent is extended or adjusted under 35 U.S.C. 154(b) by 639 days.

(21) Appl. No.: 12/864,337

(22) PCT Filed: Jan. 26, 2009

(86) PCT No.: PCT/EP2009/000484
§ 371 (c)(1),
(2), (4) Date: Oct. 1, 2010

(87) PCT Pub. No.: WO2009/092616
PCT Pub. Date: Jul. 30, 2009

(65) Prior Publication Data
US 2011/0015697 A1 Jan. 20, 2011

(30) Foreign Application Priority Data
Jan. 24, 2008 (GB) .................................. 0801264.3

(51) Int. Cl.
*A61N 1/04* (2006.01)
(52) U.S. Cl.
USPC ........................................... 607/50; 600/547

(58) Field of Classification Search
USPC ....................................... 607/50, 51; 600/547
See application file for complete search history.

(56) References Cited

U.S. PATENT DOCUMENTS

| 7,177,696 | B1* | 2/2007 | Pandelisev | 607/51 |
| 2006/0270942 | A1* | 11/2006 | McAdams | 600/547 |
| 2008/0027509 | A1* | 1/2008 | Andino et al. | 607/50 |

FOREIGN PATENT DOCUMENTS

| GB | 2432323 | 5/2007 |
| WO | 2004049937 | 6/2004 |

OTHER PUBLICATIONS

International Search Report of PCT/EP2009/000484 dated May 4, 2009 (3 pages).

* cited by examiner

*Primary Examiner* — Christopher D Koharski
*Assistant Examiner* — Michael Carey
(74) *Attorney, Agent, or Firm* — Miles and Stockbridge

(57) ABSTRACT

A wound healing system comprising an array of electrodes incorporated in a device for applying an electrical signal to a wound. The electrodes are configurable to form at least one composite electrode and the electrical signal is applied to the wound via the composite electrode(s). The system preferably includes means for determining the state of the wound, the electrode composition of the composite electrode(s) depending on the determined state of the wound. Advantageously, the electrode composition of the composite electrode(s) is adjustable in response to changes in the determined state of the wound.

29 Claims, 3 Drawing Sheets

ELECTRICAL WOUND HEALING SYSTEM AND METHOD

CROSS REFERENCE TO RELATED APPLICATIONS

This application is a §371 National Stage Application of PCT/EP2009/000484 filed Jan. 26, 2009 which claims priority to GB 0801264.3 filed Jan. 24, 2008.

FIELD OF THE INVENTION

The present invention relates to electrical wound healing systems and methods.

BACKGROUND TO THE INVENTION

It is believed that the rate of wound healing can be enhanced by electrostimulation, i.e. the application of a therapeutic electrical signal, or waveform, to the wound. Conventionally, the electrical signal is applied by two electrodes, one placed on either side of the wound. A problem with this approach is that the electrical signal is applied across the whole of the wound regardless of tissue type or stage of healing.

It is also believed that healing is enhanced if the two electrodes are placed one on either side of a wound boundary, the electrodes being shaped to closely follow the contours of the wound. In this way, the two electrodes create an optimal wound-healing electrical field across the wound edge. However, achieving suitably shaped electrodes is not feasible with standard electrode systems.

It would be desirable to mitigate the problems outlined above.

SUMMARY OF THE INVENTION

A first aspect of the invention provides a wound healing system comprising means for generating an electrical signal; an array of electrodes incorporated in a device for applying said electrical signal to a wound; means for creating at least one composite electrode from at least one of said electrodes in the array; and means for causing said electrical signal to be applied to said wound via said at least one composite electrode.

The preferred creating means creates said composite electrodes by electrically connecting together the, or each, electrode of the array that is to form part of the respective composite electrode. To this end, the creating means may include a switching device arranged to selectably connect (at least electrically) each array electrode to one or other of a positive and a negative terminal by which said electrical signal is applied in use to the composite electrodes.

The system typically also comprises a controller arranged to control the setting of said switch device, for example by means of a multiplexer. The controller may also be arranged to cause said electrical signal to be applied to said composite electrodes and, preferably, also to generate said electrical signal (in association with other circuitry if necessary, e.g. a pulse generating circuit, or other signal generating circuit).

Preferably, the system is arranged to cause a respective one or more electrodes to form the respective first and second composite electrodes depending on a desired shape, size and/or location of the respective composite electrodes.

The system may include means for selecting said respective one or more electrodes for forming the respective first and second composite electrodes. The selection is advantageously based on information concerning the state of the wound. This information may for example be provided to the system by a user via a user interface, and/or by a wound monitoring system.

In preferred embodiments, the system includes, or is in communication with, a wound monitoring system. The wound monitoring system may comprise means for measuring one or more electrical characteristics of the wound; and means for analysing the, or each, measured electrical characteristics to determine the state of the wound. Conveniently, the measuring means includes, or at least employs, the electrode array. A suitable wound monitoring system is disclosed in International PCT patent application WO 2004/049937. Alternative wound monitoring systems may be employed and do not necessarily need to use the electrode array.

In such embodiments, the system may operate in a first mode of operation, in which said electrical signal is applied to the composite electrodes for the purpose of enhancing wound healing, and a second mode of operation, in which the state of the wound is monitored.

The controller may be arranged to perform some or all of the processing mentioned above, e.g. the selection of electrodes, the measuring of electrical characteristics and/or the analysing of the measured electrical characteristics. In preferred embodiments, however, the controller is in communication with a computer arranged to perform some or all of these tasks.

In preferred embodiments, the system is arranged to create one of said composite electrodes from one or more array electrodes that are determined to be located, in use, over one or more wounded portions of the tissue and/or skin underlying the array in use, e.g. portions that are determined to be relatively damaged or unhealthy. Preferably, said one composite electrode is created to substantially fill the, or each, wounded portion.

Conveniently, the other of said composite electrodes is created from one or more array electrodes that are determined to be located, in use, outside of said one or more wounded portions. Preferably, said other of the composite electrodes is created only from electrodes that are determined to be located at, or substantially at, an edge of the, or each, wounded portion.

Alternatively, the system is arranged to create one of said composite electrodes from one or more array electrodes that are determined to be located, in use, at one side of one or more wounded portions of the tissue and/or skin underlying the array in use, the other of said composite electrodes being created from one or more array electrodes that are determined to be located, in use, at the opposite side of said one or more wounded portions.

Preferably, the system is arranged to adjust the electrode composition of said composite electrodes depending on determined changes in the state of the wound.

The polarity of the applied electrical signal, and/or one or more other characteristics of the applied electrical signal may also be selected and/or changed depending on the determined state of the wound and/or on determined changes in the state of the wound.

The array typically comprises a two dimensional array electrodes, preferably arranged in a substantially rectangular shape. The array should comprise at least three electrodes, but typically comprises at least twenty five electrodes.

In typical embodiments, the electrode array is incorporated into a wound dressing.

A second aspect of the invention provides method of healing a wound, the method comprising applying an array of electrodes to a wound; creating at least one composite electrode from at least one of said electrodes in the array; and causing said electrical signal to be applied to the wound via said at least one composite electrode.

The present invention is particularly concerned with treating and monitoring wounds in a subject's skin, and therefore also in the tissue that forms the skin, not just the outer layer of skin. Accordingly, references herein to skin are intended to embrace both any tissue that may be damaged or exposed when skin is wounded. References herein to tissue are intended to embrace any tissue that may be damaged or exposed when skin is wounded.

Further advantageous aspects of the invention will become apparent to those ordinarily skilled in the art upon review of the following description of a specific embodiment and with reference to the accompanying drawings.

BRIEF DESCRIPTION OF THE DRAWINGS

An embodiment of the invention is now described by way of example and with reference to the accompanying drawings in which.

DETAILED DESCRIPTION OF THE DRAWINGS

Figure 1:
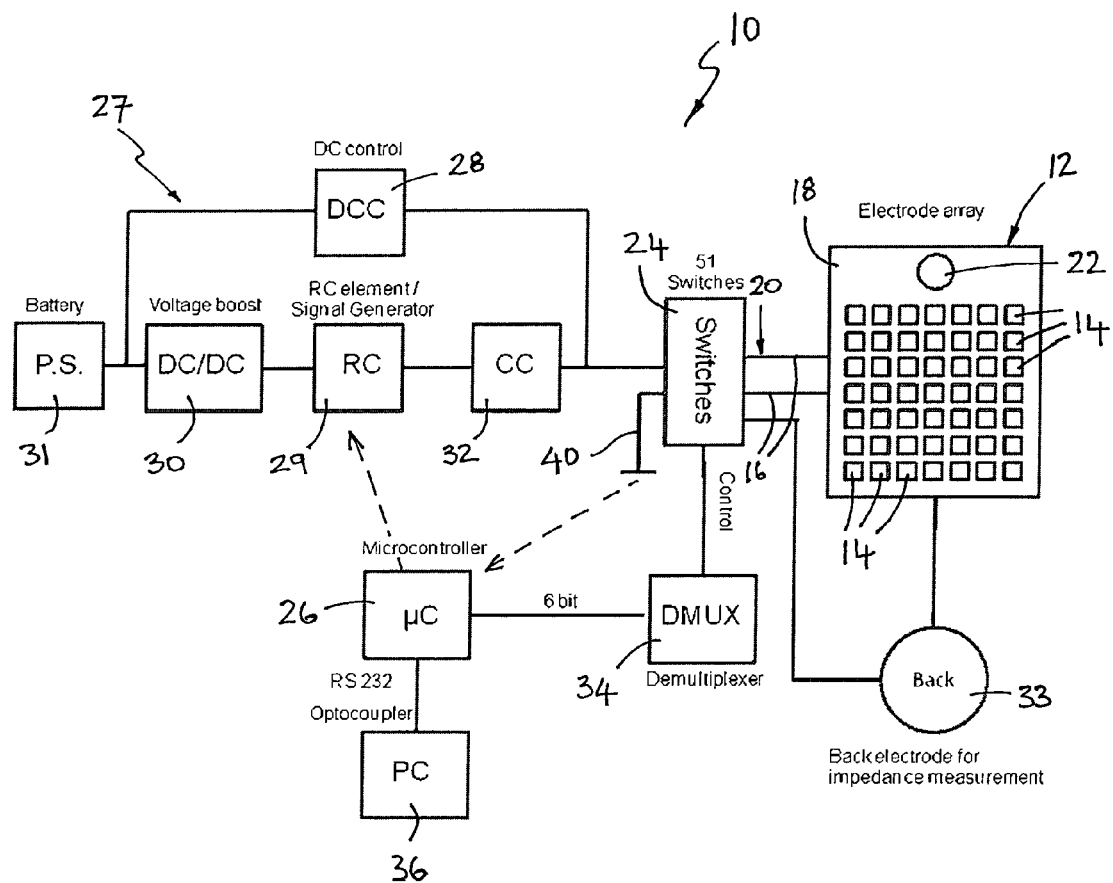
FIG. 1 is a block diagram of a wound healing system embodying one aspect of the invention.

Referring now to FIG. 1 of the drawings, there is shown, generally indicated as 10, a wound healing system embodying one aspect of the invention. The system is particularly concerned with healing wounds formed in the skin of a patient (typically human), the wound area typically comprising one or more portions of relatively damaged or unhealthy tissue and relatively undamaged or intact skin. The system 10 comprises at least one electrode array 12 (only one shown) comprising a plurality of electrodes 14. The electrodes 14 are arranged in a two dimensional array. In the illustrated embodiment, the array 12 is a 7×7 array, although the array 12 may alternatively have more or fewer electrodes 14. The illustrated array 12 is rectangular, or more particularly square, but may take alternative shapes, e.g. substantially circular or polygonal. The distribution of the electrodes 14 within the array 12 may be regular or irregular. The electrodes 14 themselves are shown as rectangular but may take any suitable shape.

Each electrode 14 is electrically connected to a respective lead 16, or other suitable signal conductor(s), by which electrical signals may be supplied to or from the electrode 14 during use. For convenience, the leads 16 are brought together at an edge of the array 12 and incorporated into a connector 20 by which electrical signals can be sent to, or received from, the array 12. In FIG. 1, for clarity the individual leads 16 are not shown connected to each electrode 14, although some of them are shown as part of the connector 20.

Typically, the electrodes 14 are carried by a substrate 18. This may be achieved by any suitable means, for example screen printing. The electrodes 14 and leads 16 may be formed from any suitable electrically conductive material, especially conductive inks that are amenable to screen printing. The substrate 18 may be formed from any suitable material, typically an electrically insulating material, e.g. polyester. The substrate 18 may be comprised of one continuous sheet (as illustrated) or may be provided in strips, each strip carrying one or more electrodes. In either case, the electrodes 14 in the array 12 are physically, or spatially, close to one another such that they form part of a common device for applying electrical signals to a localised area, in particular a wound.

By way of example, further details concerning the formation of a suitable electrode array may be found in International PCT patent application WO 2004/049937, which discloses a 'smart dressing' system that enables the monitoring of a wound site using a multi-electrode array incorporated into the dressing. The system of WO 2004/049937 differentiates between intact skin and a wound by measuring, for example, the impedance under each electrode on the array. The resulting data can be used to generate a wound map according to, for example, the relative magnitudes of the measured skin impedances.

Optionally, one or more reference electrodes 22 (only one present in the illustrated embodiment) may be provided. The, or each, reference electrode 22 is conveniently provided on the array 12, in any suitable manner, preferably adjacent the array 12. The reference electrode 22 may be used to provide a reference signal for impedance measurements as, for example, is described in more detail in WO 2004/049937.

The array 12, including the substrate 18 and, when present, the reference electrode(s) may be incorporated into a wound dressing. This may be achieved in any suitable manner, for example as described in WO 2004/049937.

The electrodes 14, 22 are electrically connected to the rest of the system 10 via the connector 20. Any other suitable means for electrical communication between the electrodes 14, 22 and the system 10 may be used in which case some or all of the leads 16 may be dispensed with.

The system 10 includes means for applying an electrical signal to one or more of the electrodes 14 simultaneously. In one mode of use, the electrical signal comprises a therapeutic signal, for example an iontophoretic signal, or other signal used in the electrostimulation of wounds. The signal is generated by a signal generating apparatus which, in the illustrated embodiment, comprises a signal generating circuit 27 under the control of a controller 26. In this example, the controller 26 conveniently takes the form of a suitably programmed microcontroller, although it may alternatively take other forms. The illustrated signal generating circuit 27 comprises a signal generator 29, a voltage booster 30, a current controller 32, and a DC controller 28. A power supply 31, e.g. in the form of a battery, is also provided to supply electrical power to the circuit.

The signal generating circuit 27 is advantageously capable of generating a range of adjustable waveforms (e.g. continuous, pulsed, square wave current/voltage etc.). By way of example, the signal generating circuit may comprise a pulse generating circuit that enables the adjustment of amplitude, frequency and/or duty cycle. It will be understood that the circuit 27 of FIG. 1 is not limiting and that a variety of alternative signal generating circuits could be used instead.

The signal is provided to a switching device 24, the setting of which determines to which electrode(s) 14 the signal is supplied. The switching device 24 typically comprises a respective switch (not shown) for each electrode 14, the setting of which determines whether the respective electrode 14 is electrically connected to the signal generator 27 in order to receive the electrical signal, or connected to a return line 40 in order to complete the circuit, i.e. the setting of the switches in the device 24 determines whether the respective electrodes 14 act as an anode or a cathode (although depending on the composition of the composite electrodes, some of the individual electrodes 14 may not be involved in the circuit). In the present embodiment, the switching device 24 is controlled by the controller 26 using a demultiplexer 34 that allows each of the respective switches to be set individually.

In the illustrated embodiment, the controller 26 is adapted for communication with a computer 36. The computer 36 is arranged to receive data from the controller 36 (and/or via a user interface (not shown)), to analyse the received data and to determine how to configure the electrodes 14 in the array 12 (as is described in more detail hereinafter). The computer 36 may also determine the characteristics of the electrical signal to be generated by the system 10. The computer 36 then instructs the controller 36 to cause the array 12 to be configured accordingly (by means of the switching device 24) and to cause the selected electrical signal to be sent to the array 12. In this embodiment, the computer 36 and controller 26 together provide means for controlling the system 10 and, in particular, means for determining how the electrodes 14 in the array 12 are configured. To this end, the computer 36 supports appropriate computer software.

In the preferred embodiment, the computer 36 is programmed to determine, for example from data received from the array 12, the state of the tissue beneath the array 12 (e.g. which portions are damaged, which are intact and relative states in between). This allows the computer 36 to determine how to configure the array 12. By way of example, this may be achieved by a method the same or similar to that disclosed in WO 2004/049937, i.e. by differentiating between intact skin and a wound by measuring, for example, the impedance (or other electrical characteristic) under each electrode of the array. To this end, the system 10 may include an impedance analyser (not shown) the same or similar to the impedance analyser disclosed in WO 2004/049937. The impedance analyser may take the form of computer software supported by the computer 36, or may be a separate unit (not illustrated) in communication with the computer 36. It will be understood that alternative means for controlling the system 10 other than the computer 36 and controller 26 may be used. For the purposes of impedance measurement, the system 10 may also include a back electrode 33, which may be arranged and used as described in WO 2004/049937.

Communication between the controller 26 and the rest of the system 10 may be implemented by any convenient means and is indicated by broken lines in FIG. 1. In the illustrated embodiment, the controller 26 is in communication with the DC control 28 to control the circuitry 27, and with the switching device 24 to receive signals from the relevant electrodes 14 depending on the setting of the switches.

In one mode of use, the electrodes 14 are arranged into one or more groups, each group comprising one or more electrode 14. The electrodes 14 in each group are electrically connected together, or at least arranged to carry a common electrical signal. Hence, each electrode group acts as a respective single electrode and may be referred to as a composite electrode. Electrostimulation signals may then be applied via the composite electrode(s). Typically, first and second composite electrodes are defined. In typical modes of use, d.c. signals are applied to the wound and so one of the composite electrodes may be designated as the anode, and the other may be designated as the cathode. In alternative embodiments, the electrical signals applied to the wound may comprise pulses or a.c. signals.

For example, in a mode of use where the "wound" composite electrode (i.e. a composite electrode positioned in use over a wounded area of tissue and/or skin) is designated as the negative electrode, the system 10 is arranged to simultaneously supply a common electrical signal to all of the electrodes 14 in the composite cathode (positive composite electrode), the composite anode providing a signal return path to the system 10. In the illustrated embodiment, the electrical grouping, or connection, of the electrodes 14 is achieved by the switching device 24. For example, the respective switch for each electrode 14 forming part of the composite cathode is set to connect its respective electrode 14 to the signal generator 27, while the respective switch for each electrode 14 forming part of the anode is set to connect its respective electrode 14 to the return line 40.

In the preferred embodiment, one of the composite electrodes is arranged for positioning, in use, over healthy or relatively healthy skin and/or tissue and is referred to hereinafter as the "healthy electrode". The other composite electrode is arranged for positioning, in use, over damaged, or relatively damaged, skin and/or tissue and is referred to hereinafter as the "wound electrode". Advantageously, the wound electrode is shaped and dimensioned to substantially fill the, or each, portion of wounded tissue beneath the array 12. The healthy electrode may be shaped and dimensioned to substantially surround the, or each, portion of wounded tissue. The shape and dimensions of the composite electrodes are determined by the electrode(s) 14 of which they are composed. The typical arrangement is such that the composite anode is the healthy electrode, while the composite cathode is the wound electrode, although the reverse arrangement is possible.

During use, the electrode composition of the composite electrodes may be changed by the system 10. In particular, the computer 36 determines which electrode(s) 14 are to form part of the respective composite electrodes and instructs the controller 26 to cause the array 12 to be configured accordingly. For example, one or more of the respective electrode(s) 14 that make up one or both of the composite electrodes may be changed, and/or the polarity of the composite electrodes may be changed. Advantageously, changing the composition of the composite electrodes is performed in response to detected changes in the state of the wound. For example, as the wound heals, the portions of tissue that are regarded as damaged or healthy may change and so it may be desired to change the shape, size and/or position of the healthy and/or wound electrodes.

In the preferred embodiment, the system 10 is arranged to perform the wound monitoring technique described in WO 2004/049937, or a similar method of monitoring a wound. To this end, the system 10 is operable in a second mode of operation in which it measures one or more electrical characteristics of the wound, e.g. impedance, in order to provide a map of the wound. In the second mode of operation, the array 12 may for example be used in the manner described in WO 2004/049937. For example, in conjunction with the computer 36, the controller 26 configures some or all of the electrodes 14, 22, 33 (as applicable), the switch device 24, and the signal generating circuit 27, to implement any one of the wound mapping methods disclosed by WO2004/049937. Hence, the computer 36 is able to determine the state of the wound from the data provided to it by the array 12. This allows the computer 36 to determine which portions of the tissue under the array 12 are to be regarded as healthy and which are to be regarded as damaged. This in turn allows the computer 36 to select a corresponding composition for the respective composite electrodes in the first mode of operation. The selection of the composition of the composite electrodes may be achieved by any other method, for example manual selection by a user.

It will be seen therefore that it is possible to use the electrode array 12 in a wound mapping mode to locate the wound and determine its shape, and then to use this information to group electrically subsets of the array's electrodes 14 to form an optimally shaped and sized composite wound electrode and healthy electrode. In particular, electrodes 14 that are identified as being located over healthy intact skin are connected together electrically to form a single composite electrode (the healthy electrode). Electrodes 14 that are identified as being located over the wound are connected together electrically and thus form a second composite electrode (the wound electrode). This is the simplest case and assumes that the wound forms a single 'island' surrounded by healthy skin.

Given that the position, shape and size of the wound can be monitored by the wound mapping measurements, a further advantage of this approach is that the composite electrodes can be continuously or intermittently reshaped (manually or automatically by the system 10) as wound healing occurs and the wound area decreases and/or changes shape. This allows optimal targeted delivery of the therapeutic signals, i.e. a 'responsive' electrode system incorporating feedback control is provided.

Figure 2A:
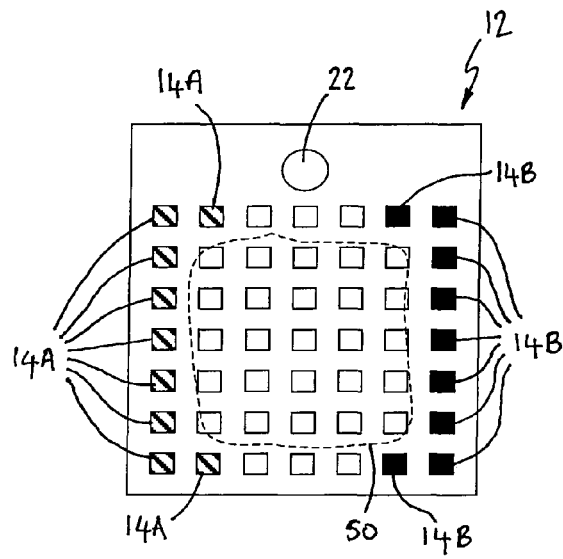
FIGS. 2A to 2D are schematic diagrams of an electrode array suitable for use in the system of FIG. 1, the array of each Figure being shown in a different configuration and superimposed on a wound.

FIG. 2A shows an example of how electrodes 14 in the array 12 on either side of a wound 50 (indicated in broken outline) can be grouped together electrically to form composite stimulation electrodes. In FIG. 2A, the electrodes 14A (shown hatched) to the left of the wound 50 are grouped electrically to form one composite stimulation electrode, while the electrodes 14B (shown with solid fill) on the right are grouped electrically to form the other composite stimulation electrode. In this case, the electrical signal is applied, in use, across substantially the entire wound 50.

Figure 2B:
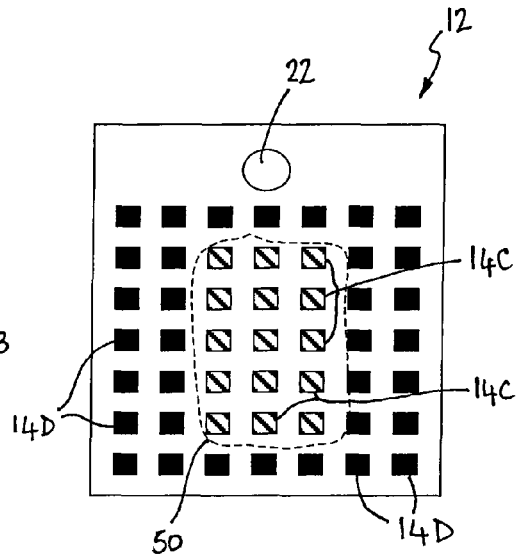

FIG. 2B shows an example of how the electrodes in the array 12 may be configured to form a "wound" composite electrode and a "healthy" composite electrode. In FIG. 2B, it is assumed that, based on impedance or potential, or related measurements made at the electrodes 14 in the second mode of operation (or by manual inspection), the wound 50 is determined to be under a group of central electrodes 14C (shown hatched). The electrodes 14C are connected electrically together in the first mode of operation to form the composite "wound" electrode. The electrodes 14D (shown with solid fill) located over intact, or relatively healthy, skin in this simplistic example, are also grouped together electrically to form the composite "healthy" electrode.

It is noted that the electrode(s) used to apply the therapeutic electrical signal, or waveform, (denoted 'healthy' electrode in the example above) could be located on any remote skin site on the patient and do not necessarily have to be formed from the array electrodes 14 located over healthy tissue. More generally, the "healthy" electrode, irrespective of polarity, may be located elsewhere on the patient and need not necessarily be implemented by the electrodes 14.

Figure 2C:
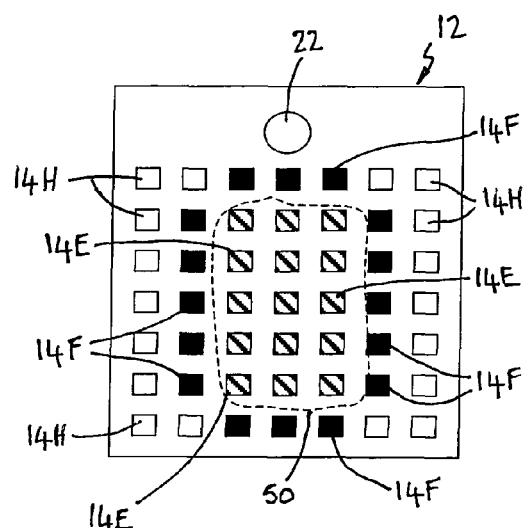

It is also noted that it is not necessary to use all of the electrodes 14 in the array 12 to form the composite electrodes. For example, only those electrodes 14 that are closest to the wound edge (on either or both sides of the wound edge) may be used to form the composite electrodes. This is illustrated in FIG. 2C where electrodes 14E (shown hatched) are those located over the wound 50 and are electrically grouped together to form the composite wound electrode. The electrodes 14H (shown with no fill) are located over intact skin and do not form part of a composite electrode in this instance. The electrodes 14F (shown in solid fill) are located at the edges of the wound 50 on the side of intact tissue. The electrodes 14F can be electrically grouped together to form a composite 'healthy' electrode that is smaller than the one shown in FIG. 2B.

Choosing only some of the electrodes that are suitable for creating the composite stimulation electrodes has the advantage of enabling the focusing of electrical current (density) in specific areas, for example under the composite cathode (electrodes 14E in this example) for increased effect, while ensuring that the current density under the composite anode (electrodes 14F in this example) is at a lower level to minimise the potentially adverse reactions which can take place.

Figure 3:
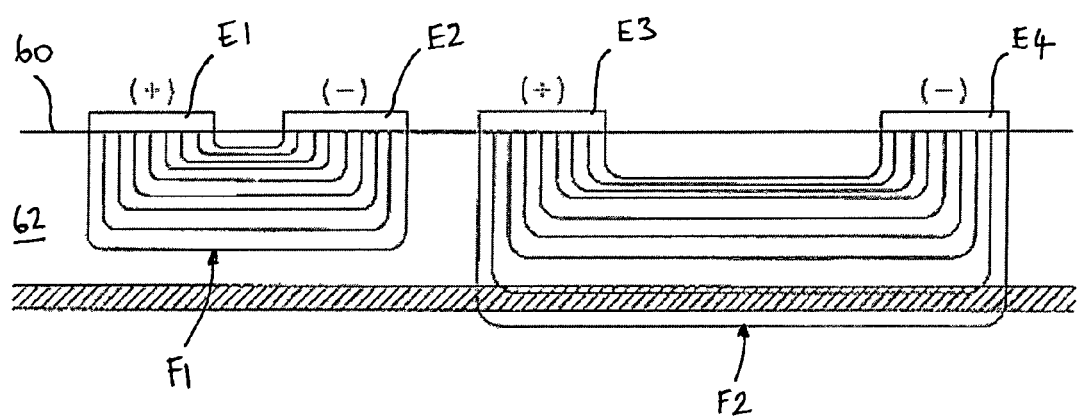
FIG. 3 is a schematic representation of the effect of inter electrode distance on the depth of penetration of the applied electrical field.

A further advantage of only using specific subsets of the electrodes that are eligible to create the composite stimulation electrodes is the ability to set the distance between the composite stimulation electrodes. For example, the inter-composite electrode distance can be set to be very close, with just the wound edge in between, to accentuate the field in this region. This is believed to be beneficial in accelerating wound healing. However, wounds vary not only in area but also in depth. The depth of penetration of the applied therapeutic electrical field can be influenced by the distance between the two composite electrodes used to apply the therapeutic signal. If the electrodes are located relatively far apart, the field penetrates more deeply than if they are relatively close together. This is illustrated in FIG. 3, which shows a first pair of relatively close electrodes E1, E2 placed on a skin surface 60. The penetration of the electrical field F1 produced by the application of an electrical signal to the electrodes E1, E2 is relatively shallow. In contrast, the electrical field F2 produced by a second pair of electrodes E4, E5, which are relatively far apart, penetrates deeper into the tissue 62.

In embodiments of the present invention, the individual electrodes 14 forming the composite 'wound' and 'healthy' electrodes can be selected to be as far apart or as close together as is necessary to set the required penetration of the electrical field into the wound to enhance healing. The selection can for example be performed by the computer 36, or may be manually selected via, for example, a user interface.

In the main body of a wound there may be 'islands' or patches of healing. In this case, combinations of electrodes 14 can be chosen manually or automatically to form appropriately sized, shaped and located composite 'wound' and 'healthy' electrodes. This allows the system 10 to produce the desired electrical field in the targeted patches. In this case, the healthy composite electrode comprises electrodes 14 located over intact skin or relatively healthy tissue that surrounds the patches of more severe wound. The wound composite electrode comprises all of the electrodes 14 located over the wound patches.

Figure 2D:
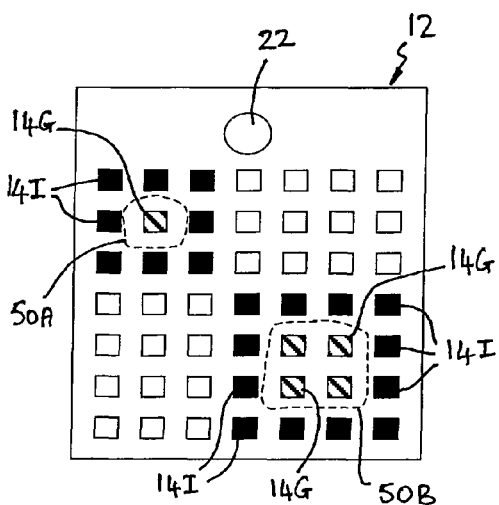

This is illustrated in FIG. 2D, in which all of the electrodes 14G (shown hatched) that are located over the wound patches 50A, 50B are electrically connected together to form one composite wound electrode. Some or all of the electrodes 14I (shown in solid fill) over the surrounding, or remaining, healthy, or relatively healthy, tissue or skin can be connected together to form the composite healthy electrode. The electrodes shown with no fill do not form part of a composite electrode in this instance.

The preferred system 10 is arranged to apply, in the first mode of operation, a range of customised electrical waveforms (e.g. d.c. or a.c., continuous, or pulsed, or square wave current/voltage signals) to pairs or selected groups of electrodes 14 in the array 12, depending on the state of the wound at any given time. To generate the signals, a pulse generator 29, for example as shown in the circuit diagram in FIG. 4, which enables the adjustment of amplitude, frequency and/or duty cycle may be used. Different types of waveforms can be applied to different areas of the wound depending on the stage of wound healing using the controlling software supported by the computer 36. The combinations of electrodes 14 used can be varied during the healing process in order to direct the therapeutic waveforms/signals to the appropriate areas of the wound. Typically, it is a cathode that is placed over the wound and an anode placed off the wound. In embodiments of the present invention, combinations of electrodes 14 can be electrically grouped together to form the composite anode, and combinations of electrodes 14 can be electrically grouped together to form the composite anode. These combinations can be chosen to best replicate the size and shape of the targeted area(s) of the wound and to produce the desired electrical field in the targeted area(s), including the desired depth of penetration in the target area(s).

Advantageously, in the second mode of operation, the system 10 performs wound monitoring to assess the state of the wound and so to provide data for use in the first mode of operation.

Although it is commonly accepted that electrical stimulation should be started with negative polarity to reduce the bacterial burden and clear the wound from sanies, there is evidence that a change in polarity is beneficial thereafter to promote further wound healing. This may in some cases be due to the wound reaching a different stage in healing which benefits more from the reversed polarity. Given that preferred embodiments of the present invention include a wound monitoring capability, the stage of healing of individual parts of the wound can be monitored in the second mode of operation and the polarity of the therapeutic signal reversed accordingly during the first mode of operation.

In the embodiment of FIG. 1, the information (e.g. impedance, and/or potential, etc.) measured at the electrodes 14 in the array 12 during the second mode of operation is analysed by the computer 36 (which may for example be a personal computer or laptop) and the best stimulation parameters are determined via an appropriate software implemented algorithm (as for example taught by WO 2004/049937). The computer 36 may calculate one or more of the following parameters relating to the therapeutic electrical signal: waveform type, polarity, frequency, amplitude and/or duration of signal. In addition, the computer 36 calculates the optimal combinations of electrodes 14 for forming the composite electrodes. By way of example, the computer 36 may compare the measured impedance values (and/or other measured characteristics) against data stored in a database (not shown) to determine appropriate parameters for the signal and/or electrode composition.

This data is then communicated to the controller 26. If desired, some or all of these parameters, and/or the composition of the composite electrodes, can alternatively be chosen manually. The controller 26 causes the supporting circuitry 27 to generate the appropriate therapeutic signal, which is amplified and applied to the appropriate electrodes 14 via the array of switches 24 which is controlled by the demultiplexer 34. The desired therapeutic signal is simultaneously (in parallel) applied through the respective individual electrodes 14 that make up the composite stimulation electrodes. Several different patches within the wound can be treated simultaneously with the requisite polarity. Additionally, it is possible to administer different therapeutic electrical signals to different wound areas, although this would typically be implemented in sequence rather than simultaneously.

Optionally, once the treatment parameters and/or other data concerning the configuration of the system are received by the controller 26, the system 10 can optionally be disconnected from the computer 36. The controller 26 may be programmed to make some adjustments to the characteristics of the applied electrical signal and/or the composition of the composite electrodes based on the measured impedance values (and/or other measured characteristics) without communicating with the computer 36.

In an alternative embodiment, the computer 36 may perform the role of the controller 26 without the need for a separate microcontroller or other device. In any event, the computer 36 is arranged for communication with the system 10 by any conventional means, preferably a wireless connection in which case the system 10 and computer 36 are equipped with suitable transceiving devices.

Optionally, the system, or at least part of it, can be incorporated into a wound dressing. In such cases, at least the array 12 is incorporated into the wound dressing. For example, in the example of FIG. 1, the signal generator 27, switches 24, electrode array 12 and power supply may be incorporated into the wound dressing. Other components, including the controller 26 and/or demultiplexer 34 and/or the computer 36, may also be incorporated into the wound dressing as appropriate. In preferred embodiments, the computer 36 is not incorporated into the dressing and communicates with the system 10 in the dressing via a wireless communication link, or other communication link, e.g. an optocoupler.

The system 10 may be incorporated into a wound dressing in the manner described in WO 2004/049937. For example, the substrate 18 may have its reverse face fixed, e.g. by means of an adhesive layer (not shown) to the dressing such that the electrodes face outwardly from the dressing. A conductive electrode gel, for example hydrogel (not shown) may be provided over the electrodes. The gel may comprise a single sheet covering all electrodes, or a plurality of gel pads, each pad covering a respective one or more of the electrodes. In the case where a sheet or pad of gel covers more than one electrode, the portions of the gel between electrodes may be rendered relatively non-conductive in order to electrically separate the relevant electrodes. The gel may also cover the leads 16, as appropriate, the leads 16 being suitably insulated.

It will be apparent from the foregoing that preferred embodiments of the invention enable the responsive and optimal targeting of wound healing electrotherapy by monitoring the wound's condition and location and using this information to select and modify the size, shape and/or location of composite electrotherapeutic electrodes and, optionally, to also modify the polarity and waveform characteristics of the applied electrotherapeutic signal. In particular, the shape of the or each composite electrode may be selected to substantially match the determined shape of the wound, especially the perimeter, or part of the perimeter of the wound. Similarly, the size of the or each composite electrode may be selected to substantially match the determined size of the wound, or wound portion, and/or the location of the or each composite electrode may be selected to substantially match the determined location of the wound, or wound portion.

The invention claimed is:
1. A wound healing system comprising:
  means for generating an electrical signal;
  an array of electrodes incorporated in a device for applying said electrical signal to a wound;
  means for creating at least two composite electrodes, each composite electrode being created from one or more of said electrodes in the array and acting as a single electrode, a size, shape or location of each composite electrode being determined by the respective electrodes in the array comprising the composite electrode; and
  means for causing said electrical signal to be applied to said wound via said at least two composite electrodes, one of said composite electrodes serving as an anode and another of said composite electrodes serving as cathode.

2. A wound healing system as claimed in claim 1, wherein the electrode composition of each composite electrode is adjustable in response to changes in the determined state of the wound.

3. A wound healing system as claimed in claim 1, further including means for determining the state of the wound, said composite electrode creating means being arranged to determine which electrodes of the array make up said at least two composite electrodes depending on the determined state of the wound.

4. A wound healing system as claimed in claim 3, wherein said means for determining the state of the wound includes:
    means for measuring one or more electrical characteristics of the wound; and
    means for analysing at least one of the measured electrical characteristics to determine the state of the wound.

5. A wound healing system as claimed in claim 3, wherein said system is operable in one mode of operation in which said wound state determining means determines the state of the wound, and another mode of operation in which said composite electrode creating means determines which electrodes of the array make up said at least two composite electrodes depending on the determined state of the wound, and in which said electrical signal is applied to said wound via said at least two composite electrodes.

6. A wound healing system as claimed in claim 1, wherein the size, shape or location of each composite electrode is determined respectively by the size, shape or location of the wound with respect to the array.

7. A wound healing system as claimed in claim 1, further including means for allowing a user to input data concerning the state of a wound.

8. A wound healing system as claimed in claim 1, further including means for allowing a user to select the one or more electrodes of the array that form each composite electrode.

9. A wound healing system as claimed in claim 1, wherein said composite electrode creating means creates said composite electrodes by electrically connecting together the electrodes of the array that form part of the respective composite electrode.

10. A wound healing system as claimed in claim 9, wherein the composite electrode creating means includes a switching device arranged to selectably connect, electrically, each array electrode to one or other of a positive and a negative terminal by which said electrical signal is applied in use to the composite electrodes.

11. A wound healing system as claimed in claim 1, wherein:
    the shape of said composite electrode serving as the anode is selected to substantially match the determined shape of the wound, or wound portion, or
    the size of said composite electrode serving as the anode is selected to substantially match the determined size of the wound, or wound portion, or
    the location of said composite electrode serving as the anode is selected to substantially match the determined location of the wound, or wound portion.

12. A wound healing system as claimed in claim 4, wherein said means for determining the state of the wound employs said electrode array to apply an electrical signal to said wound in order to measure said one or more electrical characteristics of the wound.

13. A wound healing system as claimed in claim 1, wherein the polarity of the applied electrical signal is adjustable depending on the determined state of the wound or on determined changes in the state of the wound.

14. A wound healing system as claimed in claim 1, wherein at least said electrode array is incorporated into a wound dressing.

15. A method of healing a wound of a patient by electro-stimulation, the method comprising:
    applying an array of electrodes to the wound, the array comprising a plurality of electrodes, each electrode being electrically connected to an electrical signal conductor;
    creating at least two composite electrodes, each composite electrode being created from one or more of said electrodes in the array and acting as a single electrode, a size, shape or location of each composite electrode being determined by the respective electrodes in the array comprising the composite electrode, a boundary of the wound being located between the at least two composite electrodes; and
    causing an electrical signal to be applied to the wound via said at least two composite electrodes to create an electrical field across the wound boundary, one of said composite electrodes serving as an anode and another of said composite electrodes serving as a cathode.

16. A method as claimed in claim 15, further including:
    monitoring a state of the wound; and
    adjusting the electrode composition of each composite electrode in response to changes in the determined state of the wound.

17. A method as claimed in claim 15, further including:
    monitoring a state of the wound; and
    adjusting one or more characteristics of said electrical signal in response to changes in the detected state of the wound.

18. A method as claimed in claim 15, wherein the size, shape or location of each composite electrode is determined respectively by a size, shape or location of the wound with respect to the array.

19. A method as claimed in claim 15, wherein the composite electrode serving as the anode is created from one or more electrodes of the array that are determined to be substantially in register with said wound.

20. A method as claimed in claim 19, wherein:
    said wound comprises more than one wound portion, and
    the composite electrode serving as the anode includes, for each wound portion, one or more electrodes of the array that are determined to be substantially in register with the respective wound portion.

21. A method as claimed in claim 20, wherein said one or more array electrodes of the array are selected such that the composite electrode serving as the anode substantially fills said wound or the respective wound portion.

22. A method as claimed in claim 15, wherein the composite electrode serving as the cathode is created from one or more electrodes of the array that are determined to be located outside of said wound.

23. A method as claimed in claim 15, wherein:
    said wound comprises more than one wound portion, and
    the composite electrode serving as the cathode includes, for each wound portion, one or more electrodes of the array that are determined to be substantially outside of the respective wound portion.

24. A method as claimed in claim 15, wherein the composite electrode serving as the cathode is created only from electrodes of the array that are determined to be located at, or substantially at, an edge of the wound or respective wound portion.

25. A method as claimed in claim 15, wherein the composite electrode serving as the cathode is created from a plurality of electrodes of the array that are determined to substantially surround said wound or respective wound portion.

26. A method as claimed in claim 15, wherein:
the composite electrode serving as the anode is comprised of one or more respective electrodes of the array that are determined to be located at one side of the wound, and
the composite electrode serving as the cathode is comprised of one or more respective electrodes of the array that are determined to be located at another side of said wound, such that in use said electrical signal is applied across said wound.

27. A method as claimed in claim 15, wherein:
said wound comprises a plurality of wound portions,
for each wound portion, the composite electrode serving as the anode is comprised of one or more respective electrodes of the array that are determined to be located at one side of the respective wound portion, and
the composite electrode serving as the cathode is comprised of one or more respective electrodes of the array that are determined to be located at another side of the respective wound portion, such that in use said electrical signal is applied across said respective wound portion.

28. A method as claimed in claim 15, further comprising:
monitoring a state of the wound with the array of electrodes and determining a change in the wound boundary;
reconfiguring at least one of the composite electrodes such that a selection of the electrodes to form the composite electrode is altered based on the change in the wound boundary; and
causing another electrical signal to be applied to the wound via the reconfigured composite electrodes such that an electrical field is created across the changed wound boundary.

29. A method of healing of a patient by electro-stimulation, the method comprising:
(a) positioning a plurality of electrodes over the wound, the plurality of electrodes being arranged in an array, the array being sized and shaped so as to cover the wound;
(b) at a first time:
(b1) monitoring a state of tissue beneath the array by using the plurality of electrodes, the monitoring including determining a boundary of the wound, the boundary separating damaged tissue within the wound from healthy tissue outside the wound;
(b2) selecting a first set from the plurality of electrodes based on the determined boundary and electrically connecting the first set together to serve as a first composite electrode, the first set being located over healthy tissue;
(b3) selecting a second set from the plurality of electrodes based on the determined boundary and electrically connecting the second set together to serve as a second composite electrode, the second set being located over damaged tissue;
(b4) applying a therapeutic electrical signal to the wound via the first and second composite electrodes, one of the first and second composite electrodes serving as a cathode and the other of the first and second composite electrodes serving as an anode, the arrangement of the first and second composite electrodes being such that the applied electrical signal creates an electrical field across said wound boundary;
(c) at a second time after said first time:
(c1) monitoring the state of tissue beneath the array by using the plurality of electrodes so as to re-determine the boundary of the wound;
(c2) re-selecting the first and second sets from the plurality of electrodes based on the re-determined boundary such that the first set remains over healthy tissue and the second set remains over damaged tissue, the re-selected first set serving as a reconfigured first composite electrode and the re-selected second set serving as a reconfigured second composite electrode, the electrodes of at least one of the first and second sets at the second time being different from at the first time; and
(c3) re-applying a therapeutic electrical signal to the wound via the reconfigured first and second composite electrodes such that the applied electrical signal creates an electrical field across said re-determined boundary.

* * * * *

UNITED STATES PATENT AND TRADEMARK OFFICE
CERTIFICATE OF CORRECTION

| | |
|---|---|
| PATENT NO. | : 8,682,442 B2 |
| APPLICATION NO. | : 12/864337 |
| DATED | : March 25, 2014 |
| INVENTOR(S) | : Eric Thomas McAdams |

Page 1 of 1

It is certified that error appears in the above-identified patent and that said Letters Patent is hereby corrected as shown below:

On the title page:

Item (73), Assignee should read as follows:

(73) Assignee: Institut National des Sciences Appliquees de Lyon, Villeurbanne (FR)

Signed and Sealed this
Eighteenth Day of November, 2014

Michelle K. Lee
*Deputy Director of the United States Patent and Trademark Office*